(12) United States Patent
Nishizawa

(10) Patent No.: US 6,312,603 B1
(45) Date of Patent: Nov. 6, 2001

(54) SOLID-LIQUID COUNTERCURRENT EXTRACTION CONTINUOUSLY SEPARATING APPARATUS

(76) Inventor: Hideyuki Nishizawa, 1-5-1, Nakazato, Kita-ku, Tokyo 114-0015 (JP)

( * ) Notice: Subject to any disclaimer, the term of this patent is extended or adjusted under 35 U.S.C. 154(b) by 0 days.

(21) Appl. No.: 09/402,892

(22) PCT Filed: Mar. 2, 1998

(86) PCT No.: PCT/JP98/00854

§ 371 Date: Dec. 30, 1999

§ 102(e) Date: Dec. 30, 1999

(87) PCT Pub. No.: WO98/46991

PCT Pub. Date: Oct. 22, 1998

(30) Foreign Application Priority Data

Apr. 15, 1997 (JP) .................................................. 9-113552

(51) Int. Cl.⁷ .................................................. B01D 15/08
(52) U.S. Cl. ..................... 210/656; 210/659; 210/198.2
(58) Field of Search ..................... 210/635, 656, 210/657, 659, 198.2

(56) References Cited

U.S. PATENT DOCUMENTS

| 4,422,941 | * | 12/1983 | Vaughan | 210/198.2 |
| 4,551,251 | * | 11/1985 | Kolobow | 210/635 |
| 4,857,187 | * | 8/1989 | Ito | 210/198.2 |
| 4,968,428 | * | 11/1990 | Nunogaki | 210/635 |
| 5,087,369 | * | 2/1992 | Tanimoto | 210/635 |
| 5,273,656 | * | 12/1993 | Anderson | 210/635 |

FOREIGN PATENT DOCUMENTS

| 61-204003 | * | 9/1986 | (JP) | 210/656 |
| 5-277303 | * | 10/1993 | (JP) | 210/656 |

* cited by examiner

Primary Examiner—Ernest G. Therkorn
(74) Attorney, Agent, or Firm—Oliff & Berridge, PLC

(57) ABSTRACT

A row of (n+m) powder containers which contain powder for chromatography and a row of (n+m) solvent containers which contain solvent for partition are arranged closely in parallel to each other. 0): A predetermined quantity of sample solution is added to the m-th solvent container from the left. 1): The powder containers and the solvent containers of the same numbers from the left in the rows are coupled with each other to form a row of (n+m) pairs of the powder containers and the solvent containers. 2): The powder and solvent of each pair are mixed and stirred until components to be separated come into partition equilibrium. 3): The powder and solvent of each pair are separated and made to exist in the original containers of each pair. 4): The pairs are decoupled to form the row of the powder containers and the row of the solvent containers again, and the rows are shifted from each other by one container in the opposite directions alternately. The steps 1)–4) are repeated, completing one process composed of the steps 0)–4)+steps 1)–4). The process is repeated. Each time the rows are shifted, the leading container containing separated sample component is removed, and a new container is added to the rear of the row to keep the number of containers in the row constant. By this method, the samples can be separated by relatively small number of partition equilibrium steps.

15 Claims, 8 Drawing Sheets

A······separation flow
B······recovery flow (a)

(b)

(a)

(b)

(c)

(a)

(b)

(a)

(b)

(c)

(a) 
(b)

(a) 
(b)

(a)

(b)

(c)

(Numerical Expression 1)

SOLID-LIQUID COUNTERCURRENT EXTRACTION CONTINUOUSLY SEPARATING APPARATUS

REFERENCE TO RELATED APPLICATIONS

This application is a 371 of PCT/JP98/00854 filed Mar. 2, 1998.

BACKGROUND OF THE INVENTION

1. Field of the Invention

The present invention relates to an apparatus for separating two or more components existent in a solvent for chromatography by combining multiple powder containers filled with multiple stationary phase powders for chromatography with multiple solvent container filled with the solvent for chromatography, and to a method using the apparatus.

2. Description of the Related Art

For the separation of a large amount of an organic compound that is difficult to be purified in large quantities by fractional distillation or fractional crystallization, there is liquid chromatography making use of a difference in partition factor between the solid phase and the liquid phase of an organic compound. This involves such economical problems that it requires a large amount of an expensive stationary-phase carrier and the recovery of a large amount of an elute. There is also fluidized stationary phase chromatography in which a stationary phase is added continuously to cause a liquid phase and the stationary phase to flow countercurrently to each other unlike general chromatography. This is conceptually possible but it is difficult to put it into practice.

In the case of separation by liquid chromatography, an elute generally moves and the length that the elute moves and reaches partition equilibrium is considered as one stage. Since the elute reaches equilibrium while moving, in the case of a column for preparation having a large diameter, the effective number of stages per the length of the column tends to be small.

SUMMARY OF THE INVENTION

The present invention relates to a separating apparatus for carrying out $(m+n)$-stage solid-liquid countercurrent extraction many times continuously, the apparatus comprising:

- a row of $(m+n)$ powder containers filled with stationary phase powders for chromatography, a new powder container being able to be added adjacent to the right side of a first powder container from the right of the row and a $(m+n)$-th powder container from the right being able to be removed simultaneously with, before or after the addition of the new powder container;
- a row of $(m+n)$ solvent containers filled with a solvent, a new solvent container being able to be added adjacent to the left side of a $(m+n)$-th solvent container from the right of the row and a first solvent container from the right of the row being able to be removed simultaneously with, before or after the addition of the new solvent container;
- a sample feed device for supplying a sample solution consisting of the same solvent as the above solvent and two or more components to be separated to an m-th solvent container from the right of the row of the solvent containers;
- a powder container feed device for supplying the new powder container to the right end of the row of the powder containers;
- a powder container removing device for removing a powder container from the left end of the row of the powder containers;
- a solvent container feed device for supplying the new solvent container to the left end of the row of the solvent containers; and
- a solvent container removing device for removing a solvent container in which the sample components have been separated from the right end of the row of the solvent containers, wherein
  the apparatus repeats the following stages (a), (b), (c) and (d) a required number of times,
  and to use of the apparatus making use of separation conditions obtained by the computer simulation of the following numerical expression 1;
  (a) a stage in which the sample solution is supplied to the m-th solvent container from the right for the first solid-liquid partition for the $(m+n)$-stage countercurrent extraction of the sample components, the powders and the solvent are mixed and stirred by pairing and coupling all the powder containers and the solvent containers of the same numbers from the right in the rows with each other, when partition equilibrium between solid phase and liquid phase by contact between the solvent and the powders in each of the paired powder containers is attained, the powders and the solvent in each of the paired powder containers are separated from each other and the solvent is returned to its solvent containers, and the two interconnected rows are separated from each other to complete the first $(m+n)$-stage partition between solid phase and liquid phase;
  (b) a stage in which the row of the above powder containers moves to the left by one stage, one new powder container is added to the right end of the row of the powder containers, and a powder container in which sample components have been separated is removed from the left end of the row of the powder containers, thereby forming a new row of $(m+n)$ powder containers;
  (c) a stage in which after the above sample solution is supplied to the m-th solvent container from the right for second solid-liquid partition for the $(m+n)$-stage countercurrent extraction of the above sample components or without supplying the sample solution, the powders and the solvent are mixed and stirred by pairing and coupling the powder containers and the solvent containers of the same container numbers from the right in the rows with each other, when partition equilibrium between solid phase and liquid phase by contact between the solvent and the powders in each of the paired powder containers is attained, the powders and the solvent in each of the paired powder containers are separated from each other and the solvent is returned to its solvent containers, and the two interconnected rows are separated from each other to complete the second $(m+n)$-stage partition between solid phase and liquid phase; and
  (d) a stage in which the row of the solvent containers moves to the right by one stage, one new solvent container is added to the left end of the row of the solvent containers, and a solvent container in which sample components have been separated is removed from the right end of the row of the solvent containers, thereby forming a new row of (m+n) solvent containers.

The expression "solid-liquid countercurrent extraction" means that the solid phase and the liquid phase of chromatography are contacted to each other by causing them to flow countercurrently to each other to adsorb part of the components contained in the liquid phase to the solid phase and simultaneously extract part of the components adsorbed to the solid phase into the liquid phase for the partition of these components between the solid phase and liquid phase (partition (equilibrium) of components between solid phase and liquid phase will be referred to as "partition (equilibrium) between solid phase and liquid phase" or "partition (equilibrium)" hereinafter).

The apparatus of the present invention is aimed to carry out this "partition between solid phase and liquid phase" not between a solid phase and a liquid phase which are caused to flow countercurrently to each other continuously but between a solid phase and a liquid phase which are caused to flow countercurrently to each other intermittently by partitioning among (m+n) pairs of separate containers arranged in a row. Since a liquid can be caused to stay in the containers until partition equilibrium which is preferred from a practical point of view is attained by partitioning among separate containers, the partition efficiency in each separate container is increased.

In the countercurrent extraction of the present invention, the solid phase and the liquid phase move in opposite directions as a matter of course. The expression "(m+n) stage countercurrent extraction between solid phase and liquid phase" in the present invention means that partition equilibrium in the above (m+n) pairs of separate containers, separation between solid phase and liquid phase, the disconnection of the pair and the movement of the next liquid phase (for the formation of new pairs with the solid phase of the pair at a downstream) are carried out among each pair simultaneously or almost simultaneously.

Separate containers are divided into powder containers for containing powders (or particles) corresponding to a solid phase and solvent containers for containing a solvent corresponding to a liquid phase and form pairs each of which can be separated from each other. That is, (m+n) pairs of containers are (m+n) sets of powder containers and solvent containers which can be separated from each other. Since these pairs can be separated from each other, a row of (m+n) powder containers move by one stage to an upstream of a row of (m+n) solvent containers, or the row of solvent containers move one stage to a downstream of the row of powder containers without changing the order of the containers in the row. New pairs of powder containers and solvent containers are formed each time the row of powder containers or the row of solvent containers moves and equilibrium between solid phase and liquid phase is attained each time new pairs are formed.

Partition between solid phase and liquid phase is generally carried out in the containers for containing powders. This is because the solvent can move more easily between the powder container and the solvent container than the solvent.

The temperature of partition equilibrium must be maintained at a fixed temperature because the partition coefficient (ratio) depends on temperature in most cases. The temperature of purification is a temperature at which the volatility of a liquid phase used or the compatibility between liquid phases is substantially low, for example, −10 to 60° C. The temperature is preferably a temperature which is easily maintained, for example, a temperature close to the ambient temperature of the extraction apparatus, namely, 5 to 40° C., particularly preferably 20 to 35° C.

The powders and the solvent are mixed and caused to flow in the powder container until partition equilibrium preferred from a practical point of view is attained between the powders in the powder container and the solvent from the solvent container.

When partition equilibrium between solid phase and liquid phase preferred from a practical point of view is attained, the solvent is separated from the powders and returned to the solvent container paired thereto. Thereafter, the powder container for containing the separated powders is disconnected from its paired solvent container and forms a new pair with a disconnected solvent container adjacent to the above solvent container at an upstream of the row of the solvent containers, and the powders in the powder container are mixed with the solvent of the newly paired solvent container. After equilibrium between solid phase and liquid phase is reached, separation between the powders and the solvent, the disconnection of the pair and the formation of new pairs by the one-stage movement of the powder containers to an upstream of the liquid phase are repeated similarly as described above. Thus, the solvent and the powders are caused to flow countercurrently to each other intermittently and equilibration between solid phase and liquid phase is carried out while the countercurrent of the solvent is interrupted.

The number of components to be separated is generally two but may be three or more. In the case of three or more components, when three components are represented by a, b and c, it is possible to separate the component a from the components b and c or the components a and b from the component c. The partition coefficient of one of the three components should be different from those of other two components.

The method of the present invention is suitable when the components to be separated are optical isomers contained in a racemic mixture, that is, the separation of which is completed by once resolution into each isomer.

For example, the method of the present invention is used when methylphenobarbital is separated by a triacetyl cellulose solid phase and extraction with ethanol or when oxazepam is separated using a stationary phase chemically modified with cyclodextrin.

A liquid for dissolving a sample to be separated is generally made identical to a solvent used for the separation of the present invention (to be referred to as "separation solvent" hereinafter) and use of other solvent makes conditions complicated disadvantageously.

(m+n) indicating the number of powder containers or solvent containers used for partition equilibrium is generally 10 to 1,000, preferably 20 to 100. m and n are generally equal to each other (m≠n may be used according to the result of computer simulation).

The relationship between m and n is $n-m/3 \leq m \leq n+m/3$, preferably $n-5 \leq m \leq n+5$, particularly preferably m=n.

The row of powder containers or solvent containers may be straight, curved, circumference-like, ring-shaped or zig-zag (for example, comb-like). It may be spiral. The row may not be present on the same plane and may be present on multiple planes. When the row is present on two or more planes, the row from one plane to another plane is disconnected positionally. However, when the row moves to a downstream or upstream, the disconnected container carries out the function of continuous countercurrent extraction separation by moving up or down though the row is disconnected. The paired powder containers and solvent containers may be located at a position convenient for desired extraction separation. Generally speaking, they are preferably located as close to each other as possible to facilitate pairing and the movement of the solvent.

As the stationary phase for chromatography, all stationary phases which can be used as a carrier for liquid chromatography may be used. Especially, a porous silica gel which works as an adsorption and partition agent is a typical stationary phase, and exemplified by reverse stationary phases such as ODS obtained by modifying the porous silica gel with hydrocarbon, ion exchange stationary phases, ion-free stationary phases, ion paired stationary phases, gel filtered stationary phases, affinity stationary phases and the like. It can be said that a stationary phase obtained by modifying the surface of a carrier with various substances formed for the separation of optical isomers is the most suitable for use in the method of the present invention.

The powders may be particulate. The particle diameter must be such that the powders do not pass through a filtration unit when the powders and the solvent are separated from each other by filtration. The powders generally have a particle diameter of 30 to 50 $\mu$m, especially 35 to 45 $\mu$m. It is preferred that the powders should be hardly worn away by mixing and stirring for partition equilibrium between solid phase and liquid phase.

The surfaces of the powders are preferably moistened with a separation solvent in advance.

The volume of the powder container may be such that the solvent does not overflow by stirring or shaking after the solvent enters the powder container from the solvent container for partition. It is generally 10 ml to 1,000 ml.

The shape of the powder container is generally a bottomed cylinder. The shape of the powder container can be changed according to a method of separating the solvent from the powders. For instance, when separation is carried out by filtration, the powder container has a filtration unit at the bottom, such as a filter net or molten glass filter. When separation is carried out by sedimentation such as centrifugation, whole or part of the bottom portion or several spots of the bottom portion are narrowed like an inverse cone, inversely truncated cone or inverse semi-sphere, a thin pipe is provided in the bottom portion to collect the sediment, or a recessed portion such as a groove or hole is formed in the bottom portion to remove the solvent from the powder sediment effectively and enable the powders and the solvent to be well separated from each other when the solvent is moved (or sucked).

The volume of the powders contained in the powder container is $\frac{1}{30}$ to 1 time, generally $\frac{1}{20}$ to $\frac{1}{3}$ time the volume of the solvent to be mixed for partition equilibrium. The volume may be such that it does not impede the separation of the powders from the solvent and that the mixed solution does not run out from the powder container when the powders and the solvent are mixed together for partition equilibrium.

The volume of the solvent container is sufficiently larger than the volume of a solvent used for partition equilibrium, a volume obtained by adding the volume of the above solvent and the volume of a solvent when a solution containing components to be separated is added, or a volume obtained by adding the volume of the above solvent and the volume of a portion immersed in the solvent of the powder container when the powder container is stored in the solvent container for partition equilibrium so that the solvent does not overflow by a desired operation such as the rocking or inclination of the solvent container. The volume is generally 50 ml to 2,000 ml.

The shape of the solvent container is generally a bottomed cylinder. When the powder container is placed in the solvent container for partition equilibrium, the inner surface of the solvent container is generally formed such as to be fit to the outer shape of the powder container so that the powder container contained in the solvent container can be moved easily.

The solvent is a solvent used for general chromatography, as exemplified by water, petroleum-based hydrocarbons such as hexane, aromatic hydrocarbons such as benzene, esters such as ethyl acetate, ketones such as acetone, hydrocarbon halides such as chloroform, alcohols such as ethanol, organic acids such as acetic acid, organic amines such as ethylamine, organic amino alcohols such as ethanolamine, solvents which are liquid at normal temperature, mixed solvents of substances which dissolve and become a liquid, and all solvents which have the property of partitioning a sample substance between carriers for chromatography.

The solvent may contain an optically resolving agent.

Mixing for promoting partition equilibrium is carried out by stirring, rocking, vibration or shaking. A container filled with a mixture may be inclined and rotated. An accessory for mixing can be attached or connected to the powder container and/or the solvent container as required. For instance, when a stirrer for stirring in the powder container is placed in the powder container and a rotary magnetic field or magnet for rotating the stirrer is provided on the under surface of the bottom portion of the powder container at the time of mixing. As an alternative means, a device for moving vertically the powder container having a filtration unit in the bottom at predetermined time intervals in the solvent container may be connected to the solvent container. As another alternative means, a vibrator for stirring a mixed solution of the solvent and the powders at predetermined time intervals may be connected to the outer side of the solvent container containing the powder container or the outer side of the powder container.

The separation of the powders from the solvent is carried out by standing, centrifugal force, filtration by the pressurization on the powder side or the depressurization from the solvent side, and standing or the inclination of the supernatant solvent obtained after centrifugation or the sucking of the solvent through a pipe. In the case of separation by filtration, the powder container is existent in the solvent container and the solvent is returned to the solvent container from which the solvent has been supplied. In the case of the separation of the supernatant, for the entire row, the solvent is returned to the paired solvent container or injected into the paired solvent container at a downstream by one stage in the row. In the latter case, it corresponds to that the row of the powder containers moves to an upstream of the solvent by one stage, or the row of the solvent containers moves to a downstream by one stage.

The powder container which went through (m+n) times of countercurrent extraction is disconnected from the solvent container paired therewith and removed from the row of (m+n) powder containers. At the same time, a new powder container is added to form a new row of (m+n) powder containers.

The solvent container which went through (m+n) times of countercurrent extraction is disconnected from the powder container paired therewith and removed from the row of (m+n) solvent containers. At the same time, a new solvent container is added to form a new row of (m+n) solvent containers.

The above removal and addition of a powder container or a solvent container are carried out alternatively, in general, in such as, first the powder container and then the solvent container. However, the method of the present invention does not exclude a case where the removal and addition are carried out on the same type of containers two times or more alternately, for example, a powder container, a powder container, a solvent container and a solvent container, or three times or more alternately. However, the removal and addition are preferably carried out one time alternately to fully exhibit the effect of separating the (m+n) pairs of powder containers and solvent containers and simplify separation operation.

The sample solution containing two or more components to be separated is supplied to an m-th solvent container from the right of the row of the solvent containers. The supply of this sample solution is carried out before or after first or second partition equilibrium. When countercurrent extraction is controlled by the simulation of a solid-liquid partition equilibrium expression, the sample solution is added before or after each partition equilibrium or every two times of partition equilibrium in accordance with the numerical expression. When the removal and addition of a powder container and a solvent container are carried out one time alternately, the sample solution is added before every two times of partition equilibrium to facilitate simulation and control.

It is preferred to determine the numerical value of (m+n), the concentration of each component in the sample solution, the type of the solvent, the material of the powders, the number of times of addition of the sample solution, the amount of the sample solution added, the volume of the solvent in the solvent container, the amount of the powders and the like by using a partition equilibrium expression which has been confirmed theoretically or experimentally as will be described later, preferably a theoretical partition equilibrium expression which has been experimentally corrected. It is more preferred to determine conditions by experimentally confirming a partition equilibrium expression obtained by theoretical computer simulation.

The components adsorbed to the powders in the powder container removed from the row of (m+n) powder containers and disconnected from the solvent container paired with the powder container are eluted by a commonly used method such as mixing or stirring using the'same solvent as the separation solvent. The powders can be re-used as the powders for a new powder container. When the separation solvent used for countercurrent extraction is constant and the components adsorbed to the powders are eluted with the same solvent as the separation solvent, the powders which are a stationary phase can be re-used with ease.

An elute containing the components eluted from the powders is concentrated to obtain the components adsorbed to the powders. The components may be further crystallized from the solvent and further purified as required. Since the eluting solvent is the same as the separation solvent, recovery and control are easy.

The adsorbed components can be eluted from the powders in the powder container to be removed from the row of the powder containers by partition equilibrating the powders with the eluting solvent a desired number of times while the powders are contained in the powder container. With this method, labor and time required to wash away the powders from the powder container and to charge the powders into another powder container by metering can be omitted. In addition, as the components can be eluted using the same solvent as the separation solvent by the same method as the countercurrent extraction method of the present invention, both ends of the countercurrent extraction flow of the present invention are connected to each other to form a loop in the stage of the elution of the components from the powders in the powder container, thereby making it easy to stabilize the countercurrent extraction flow of the present invention.

As described above, the solvent container which went through (m+n) times of countercurrent extraction is disconnected from the powder container paired therewith and removed from the row of (m+n) solvent containers. The solute in the disconnected solvent container, that is, the separated components in the solution are obtained by concentrating and drying the solution. Thereafter, the components are purified by a commonly used method, for example, crystallization from the solvent as required.

When the number of components to be separated is 3 or more, there is a possibility that two or more components are contained in the powders in the powder container or the solvent in the solvent container which has gone through (m+n) stage countercurrent extraction. In this case, the components can be further separated by the separation method of the present invention or by a commonly used purification method.

Further, the separation of the powders from the solvent after partition equilibrium is reached is carried out by filtration or the separation of the supernatant, as described above.

Separation by filtration is carried out by standing, centrifugal force, the pressurization on the powder side or the depressurization from the solvent side. In the case of separation by standing, after partition equilibrium is reached in the powder container, the powder container is raised to an appropriate height in the solvent container. The solvent in the powder container is passed through a filtration unit provided in the bottom of the powder container and flows down or drops down into the solvent container. The time when dropping ends is the time when separation is completed.

However, as the solvent cannot be separated from the powders quickly only by standing, it is preferably separated by centrifugal force, the pressurization on the powder side or the depressurization from the solvent side.

In the case of separation by centrifugal force, after partition equilibrium is reached, the powder container is raised to an appropriate height in the solvent container and part of the solvent is dropped from the powder container at that position by standing as required and then the powder container and the solvent container are both centrifuged in such a manner that the bottom of the powder container does not touch the liquid surface of the solvent in the solvent container, thereby promoting the separation of the powders from the solvent.

For centrifugation, (m+n) powder containers and (m+n) solvent containers are arranged in a ring-form. When the powder containers are existent in the respective solvent containers after partition equilibrium is reached, each of the paired powder containers can be centrifuged such that it can leave from the liquid surface of the solvent in the solvent container at that position in the ring-form. Thus, the operation is easy (the solvent container containing the powder container can be inclined together with the powder container by centrifugal force at the time of centrifugal operation). Since the solvent does not evaporate or there is no vaporization caused by an air stream generated by the following pressure difference at the time of separation, concentration fluctuations caused by the concentration of the solvent have no influence upon partition equilibrium.

In the case of the pressurization on the powder side or the depressurization from the solvent side, that is, a pressure difference, after partition equilibrium is reached, the powder container is raised to an appropriate height in the solvent container, part of the solvent is dropped down from the powder container by standing as required at that position and then the separation of the powders from the solvent is promoted by pressurizing the powder container with air or nitrogen gas or depressurizing the solvent container side of the filtration unit of the powder container.

As a modification of the method of promoting separation by a pressure difference, a filtration unit is provided in the bottom of the powder container, the powder container and the solvent container are both made a bottomed cylinder, and an airtight portion is formed on the solvent container side of the filtration unit so that at least part of the outer side wall of the powder container and at least part of the inner side wall of the solvent container can be brought into close contact with each other in a looped belt form and perpendicular to the cylindrical axis. The outer side wall and the inner side wall can slide and reciprocate over the width of the belt at this close contact portion and the solvent in the solvent container can pass and reciprocate through the filtration unit of the powder container by depressurization or pressurization caused by this reciprocation. By the reciprocation of the solvent, the powders and the solvent are stirred and mixed together. When the bottom portion having the filtration unit of the powder container is raised to an appropriate height using this device, the separation of the powders from the solvent is promoted by the depressurization of the solvent container. The advantages of the device are that mixing and separation can be carried out using the same device and that a pressurization device or depressurization device or pipe is not required to generate a pressure difference. The device has still another advantage that the solvent on the powders does not evaporate by gas passing through the filtration unit because the gas reciprocating through the filtration unit is saturated with solvent vapor.

The inner wall of the solvent container can have a looped belt-like recess at a position higher than a portion which the looped belt-like close contact portion passes and the side wall of the powder container can have holes at positions higher than the highest liquid level of the solvent during the mixing of the powders and the solvent so that the solvent does not leak to the outside from the air tight portion through the above looped belt portion. This looped belt-like recess can be formed by increasing slightly the inner diameter of the solvent container. The solvent which rises up the close contact surface as a lubricant when the outer side wall and the inner side wall slide over the close contact portion and reciprocate over the width of the belt can flow from the looped belt-like recess in the solvent container and can be refluxed to the powder container from the holes in the powder container. Thereby, the solvent leaking from the close contact portion can be recovered.

In the case of separation by inclining the solvent which is a supernatant after standing or centrifugation or sucking the solvent through a pipe, the solvent is returned to the solvent container from which the solvent has been supplied or charged into the paired solvent container of the next stage at a downstream as described above. This means that the row of the powder containers moves by one stage to an upstream of the solvent, or the row of the solvent containers move by one stage to a downstream.

To quicken the sedimentation of the powders, separation by centrifugation is preferably carried out. Preferably, whole or part of the bottom portion or several spots of the bottom portion are narrowed like an inverse cone, inversely truncated cone or inverse semi-sphere, a thin pipe is provided in the bottom portion to collect the sediment, or a recessed portion such as a groove or hole is formed in the bottom portion so that the supernatant can be separated from the powder sediment easily and the powder sediment can be contained at a high density. That is, a groove or inverse conical hole for storing the sedimented powders (the upper area of the groove or hole is much smaller than the bottom area of the powder container. For example, it is $\frac{1}{5}$ to $\frac{1}{30}$ of the total bottom area) is preferably formed in the bottom portion of the powder container. Since the area of the groove or hole is much smaller than the bottom area of the powder container, the sediment deposits at a high density by centrifugal force, forces out the solvent between deposited powders and occupies only the narrow portion of the bottom portion of the powder container. Thus, the amount of the powders which are moved together with the sucked solvent is greatly reduced. Consequently, the solvent is easily sucked out without being accompanied by the powders. The powders contained in the groove are easily mixed with the solvent by vibration for helping mixing when they are mixed with the solvent for next partition.

A small amount of powders accompanying the solvent can be removed by providing a filtration unit on the route of a pipe for sucking out the solvent or a filtration unit which extends from the inner surface of an upper portion of the powder container (close to the inlet) to the center of the powder container. The powders deposited on this filtration unit are returned to the powder container by a back flow of the solvent from the next solvent container paired with the powder container for the next partition and hence, rarely affect partition equilibrium.

When (m+n) powder containers and (m+n) solvent containers are looped at the time of centrifugation, only the powder containers can be centrifuged at where they are. Therefore, the operation is easy. Centrifugation without filtration has such an advantage that the particle diameter of the powder is not limited by the diameter of a filter pore and very fine powders can be used. Silica gel or the like used as a stationary phase for chromatography is porous and an effectively working surface is not only the surface of a stationary phase powder. However, since the solution reaches the inner surface of a pore more quickly as the size of the powder becomes smaller, the partition equilibrium reach time becomes short but the effective area does not change so much. Therefore, when the particle diameter is large, it can be handled merely by elongating the stirring time.

Since the solvent is not evaporated by an air stream generated by a pressure difference caused by depressurization seen in vacuum filtration at the time of solid-liquid separation, concentration fluctuations caused by the concentration of the solvent do not affect partition equilibrium.

The operation of the apparatus of the present invention is preferably carried out using the following partition equilibrium expression. A method of calculating solid-liquid countercurrent extraction separation using the partition equilibrium expression will be described hereinafter.

This method is a method of purifying organic compounds steadily and continuously comprising the steps of:

repeating multi-stage extraction between solid phase and liquid phase by causing the solid phase and liquid phase to flow countercurrently to each other in the separation unit of a purifying apparatus consisting of the separation unit and a recovery unit so as to separate a mixture of organic compounds into two groups according to partition coefficients between two phases and extract and recover a group of purified organic compound(s) into the solid phase in multiple stages;

repeating multi-stage extraction between the phases in the recovery unit from the solid phase containing the purified organic compound(s) with another fresh liquid phase than the liquid phase used in the separation unit simultaneously with the above extraction; and supplying the solid phase from which the organic compounds have been recovered to the above separation unit to be recycled, wherein:

the number of stages of extraction in the separation unit is (m+n);

a sample solution contains an organic compound of interest to be purified and at least one organic compound different from the organic compound, the sample solution to be supplied for each time of extraction contains f g of a solvent which is a liquid phase and the organic compounds of interest to be purified in an amount (single substance) M(mg)=fC (mg) (C mg is the amount of each of the organic compounds based on 1 g of the solvent) and is supplied to the liquid phase of the m-th extraction stage of the separation unit each time extraction is made;

H g of the solvent which is the liquid phase is supplied to the (m+n)-th extraction stage which is the final extraction stage of the separation unit each time extraction is made;

S g of the solid phase is supplied to the first extraction stage of the separation unit from the recovery unit each time extraction is made;

the solid phase discharged from the (m+n)-th extraction stage of the separation unit is supplied as it is to the first stage of the recovery unit;

the number of extraction stages of the recovery unit is p;

Hr g of the above another fresh liquid phase B is supplied to the p-th extraction stage which is the final extraction stage of the recovery unit each time extraction is made and passes through each extraction stage of the recovery unit and recovers the above purified organic compound(s) from the solid phase by multistage extraction, and the Hr g is discharged from the first extraction stage of the recovery unit each time extraction is made;

S g of the solid phase from which the purified organic compound(s) have been recovered and removed is discharged from the p-th extraction stage which is the final extraction stage of the recovery unit each time extraction is made and supplied to the first stage of the separation unit; and the organic compounds of interest to be purified are purified steadily by setting the ratio of H and S in extraction separation conditions to ensure that the ratio of Wr(1) and W(1) of one of the two organic compounds of interest to be purified satisfy Wr(1)>>W(1) and those of the other organic compound satisfy Wr(1)<<W(1), the values Wr(1) and W(1) obtained by the computation of an equilibrium expression which gives the values of partition coefficient at each-stage concentration of H, S, f, C, Hr, p, m and n in the equilibrium expression and the compounds of interest to the following extraction equilibrium expression (numerical expression 1) in which the number of estimated extraction stages (m+n) and the partition coefficient D(n) of the organic compounds of interest to be purified between the solid phase and the liquid phase at the concentration of an extraction stage (n-th stage) where the liquid phase is present:

The numerical expression is listed in FIG. 9.

[wherein the numerals in rectangles at the center indicate the extraction stage numbers of the separation unit or the recovery unit (for example, n indicates an n-th extraction stage), the numerals within the parentheses indicate the extraction stage numbers where the corresponding liquid phases are present, E(m+n) indicates D(m+n)·(S/H), D(m+n) indicates the partition coefficient of an organic compound to be purified in an (m+n)-th extraction stage, H indicates the amount of a liquid phase (unit: g) to be supplied to the (m+n)-th extraction stage which is the final extraction stage of the separation unit, which is given before the following computation or obtained by the computation, S indicates the weight (unit: g) of a solid phase discharged from the p-th extraction stage of the recovery unit and supplied to the first extraction stage of the separation unit, which is given before the following computation together with H or obtained by the following computation, fC signifies the amount (unit: mg) of an organic compound to be purified in the sample solution supplied, which is obtained by the following computation or given before the computation, f signifies the supply amount (unit: g) of a liquid phase B in the sample, which is obtained by the following computation or given before the following computation, G(m) signifies D(m)·[S/(H+f)], D(m) signifies the partition coefficient at the concentration of the organic compound of interest to be purified in the m-th extraction stage of the separation unit, b(m) signifies the content of the organic compound of interest to be purified in the solid phase in the m-th extraction stage of the separation unit, w(m) signifies the content of the organic compound of interest to be purified in the liquid phase B in the m-th extraction stage of the separation unit, Hr represents the liquid amount (unit: g) of a fresh liquid phase to be supplied to the p-th extraction stage which is the final extraction stage of the recovery unit, which is given before the following computation together with H or obtained by the following computation, Er(p) represents Dr(p)·(S/Hr), Dr(p) represents the partition coefficient of the organic compound of interest to be purified in the p-th extraction stage of the recovery unit, br(p) represents the content of the organic compound of interest to be purified in the solid phase in the p-th extraction stage of the recovery unit, and wr(p) represents the content of the organic compound of interest to be purified in the liquid phase B in the p-th extraction stage of the recovery unit], and one of the organic compounds of interest is taken out as W(1) and the other as Wr(1).

The extraction separation apparatus which is the separation unit used in this purification method has a sample injection unit in an m-th stage from the bottom and (m−1) extraction stages below the m-th stage and n extraction stages above the m-th stage with the injection unit interposed therebetween, all the extraction stages being numbered 1 to m and (m+1) to (m+n) from the bottom, as shown in the numerical expression 1.

An extraction recovery device which is the recovery unit used in this purification method has p extraction stages.

To consider operation conditions theoretically, when operation is carried out by interconnecting the separation unit and the recovery unit under arbitral conditions, the amount (unit: g) of the compound of interest to be purified which is discharged from each extraction stage in unit time, accompanied by the solid phase of the stage, is represented by b(1), b(2), ... b(m), b(m+1), ... b(m+n) in the separation unit and br(1), br(2) ... br(p) in the recovery unit, and the amount (unit: g) of the compound of interest to be purified which is discharged from each extraction stage in unit time, accompanied by the liquid phase, is represented by w(1), w(2) ... w(m), w(m+1), ... w(m+n) in the separation unit and wr(1), wr(2), ... w(p) in the recovery unit.

Further, the value of partition rate which changes in accordance with the concentration of the compound of interest contained in the liquid phase in each extraction stage is represented by D(1), D(2), ... D(m), D(m+1), ... D(m+n) in the separation unit and Dr(1), Dr(2), ... Dr(p) in the recovery unit.

An object of the present invention is, in order to obtain readily, stably and most effectively the organic compound of interest to be purified (to be referred to as "compound of interest" hereinafter) having the target purity and the target output when this purifying apparatus consisting of the separation unit and the recovery unit is operated, to find which values should be set as the concentration C mg of the compound of interest in the sample solution supplied based on 1 g of the solvent (concentration in the liquid phase of the sample solution) and the flow rate fC mg of the liquid phase as the solvent of the sample solution according to the amount S g of the solid phase recycled each time, the amount H g of the liquid phase supplied each time to the separation unit and the amount Hr g of the liquid phase supplied each time to the recovery unit, or which values should be set as the above amounts H and Hr g of the liquid phase supplied each time and the amount S g of the solid phase recycled each time according to the concentration C mg of the compound of interest in the sample solution supplied based on 1 g of the solvent (concentration in the liquid phase of the sample solution) and the amount f g of the liquid phase supplied each time.

A detailed description is subsequently given of the contents of the equilibrium expression 1 and how to set operation conditions.

The purifying apparatus is such as shown in expression 1 that the sample solution is injected into the m-th extraction stage of the separation unit. Although the recovery unit having p extraction stages is depicted above the separation unit, the actual position relationship between the separation unit and the recovery unit is not limited to this and may be this, or the separation unit and the recovery unit may be arranged in parallel, or the recovery unit may be arranged below the separation unit. The solid phase moves between the separation unit and the recovery unit.

S g of the solid phase (which may have optically resolving capability) is supplied to the first extraction stage of the separation unit each time extraction is made, passed through the separation unit and the recovery unit and then recycled and returned to the original position. In contrast to this, Hr g of a fresh liquid phase for recovery is injected into the final extraction stage of the recovery unit each time, passed through the recovery unit alone and discharged to the outside of the purifying apparatus. H g of the liquid phase for separation is injected into the final extraction stage of the separation unit, passed through the separation unit alone, discharged to the outside of the purifying apparatus and recovered.

The sample solution contains a compound of interest to be purified and one or two or more of organic compounds different from the compound of interest. The sample solution supplied for each extraction contains f g of a solvent as a liquid phase and C mg of the compound of interest based on 1 g of the solvent and is supplied to the m-th extraction stage of the separation unit. As a result, the amount of the liquid phase supplied to stages downstream from the sample injection position and after is (H+f) g each time extraction is made. The compound of interest is extracted into the solid phase discharged from the separation unit (thereafter, the compound of interest is extracted from the solid phase by the solvent in the recovery unit) or into the liquid phase discharged from the separation unit, then separated and recovered.

[material balance in each extraction stage of recovery unit]

Under such conditions that partition equilibrium is established, when the amount of the residual compound of interest discharged together with the solid phase from the p-th extraction stage of the recovery unit to be recovered is represented by br(p), the amount wr(p) of the compound of interest discharged together with the liquid phase from this extraction stage is obtained from the following equation:

$$wr(p)=br(p)/Er(p)$$

(Dr(p) indicates a partition rate: Dr(p)=(concentration of sample substance in solid phase)/(concentration of sample substance in liquid phase), and Er(p), the extraction coefficient, is expressed as Er(p)=Dr(p)·S/Hr).

Since the partition rate between solid phase and liquid phase of the organic compound of interest has concentration dependency when the concentration range is wide, the partition rate at several points of the concentration of the organic compound of interest within the range which can be estimated in the separation unit and the recovery unit is actually measured and given to a computer for computing an equilibrium expression as a basic condition.

When the material balance of this extraction stage is taken into consideration, the following expression is established.

$$br(p-1)+wr(p+1)=wr(p)+br(p)$$

Since the sample is not contained in a liquid phase newly injected into the extraction stage (p) and wr(p+1)=0, the following expression is obtained.

$$br(p-1)=wr(p)+br(p)$$

Further, the amount of the compound of interest discharged by the liquid phase from the extraction stage (p−1) is obtained from the following expression as in the case of the p-th stage.

$$wr(p-1)=br(p-1)/Er(p-1)$$

The following expression is obtained from the material balance in the extraction stage (p−1) and the extraction stage (p).

$$br(p-2)=wr(p-1)+br(p)$$

The same computation is continued up to the first stage of the extraction device for recovery to obtain the amount wr(1) of the compound of interest recovered in unit time by the recovery unit from the following expression:

$$wr(1)=br(1)/Er(1)$$

and the amount br(0) of the sample supplied to the recovery unit from the separation unit from the following expression:

$$br(0)=wr(1)+br(p).$$

[amount of compound of interest discharged from each extraction stage of separation unit]

Meanwhile, as for the total material balance of the separation unit, since the amount of the compound of interest supplied to the separation unit and the amount of the compound of interest discharged from the separation unit are equal to each other, the following expression is established.

$$fC+br(p)=b(m+n)+w(1)$$

Since the solid phase moved from the separation unit is directly supplied to the recovery unit, the following expression is established.

$$b(m+n)=br(0)$$

Since the solid phase discharged from the recovery unit is used as the solid phase of the separation unit as it is, the following expression is established.

$$b(0)=br(p)$$

[state of portion of separation unit in upstream from sample solution injection portion]

The solid phase discharged from the final extraction stage (m+n) of the separation unit is extracted by a new liquid phase in the final extraction stage of the separation unit. The amount w(m+n) of the compound of interest discharged into this liquid phase is obtained by dividing the discharge amount b(m+n) of the compound of interest in the solid phase by an extraction coefficient E(m+n) which is based on the concentration of the liquid phase in this extraction stage (E(m+n)=D(m+n)·S/H) (wherein D(m+n) indicates a partition rate).

$$w(m+n)=b(m+n)/E(m+n)$$

The material balance of the extraction stage (m+n) gives the following expression:

$$b(m+n-1)=w(m+n)+b(m+n)$$

When computation is continued in the same manner as in the above example to calculate the concentration of the compound of interest in the solid phase flowing into the extraction stage (m+1), the following expression is obtained.

$$b(m)=w(m+1)+b(m+n)$$

[state of portion in down stream from sample solution injection portion]

Since the amount of the compound of interest in the liquid phase discharged from the separation unit is equal to a difference between the amount of the compound of interest introduced into the separation unit and the amount of the compound of interest discharged into the solid phase, the following expression is established.

$$w(1)=fC+b(0)-b(m+n)$$

The amount of the compound of interest in the solid phase equilibrated with this by the extraction of the extraction stage (1) is obtained by multiplying the amount of the compound of interest in the liquid phase by an extraction coefficient G(1) (G(1)=D(1)·S/(H+f)) (D(1) indicates a partition rate).

$$b(1)=w(1)\cdot G(1)$$

When the material balance of this stage is taken into consideration, the following expression is obtained.

$$w(2)=b(1)+w(1)-b(0)$$

When the amount of the compound of interest in the solid phase discharged from the m-th stage is obtained by computing extraction equilibrium and material balance in each stage in the same manner as in the above example, the following expression is obtained.

$$b(m)=w(m)\cdot G(m)$$

When the number of stages of the separation unit in the above apparatus is (m+n) and the number of stages of the recovery unit is p, D(n) and D(r) indicate the partition coefficients of the substances of interest and a fixed value is given depending on a solvent system used. Therefore, br(p), wr(1), w(1), the amount [fC(mg)] of the compound of interest supplied, the amount [f(g)] of the solvent supplied in the sample solution, the amount [Hr(g)] of the solvent for recovery supplied to the recovery unit, and the correlation between the amount [H(g)] of a heavy solution and the amount [S(g)] of a light solution supplied to the separation unit are determined by the above method.

Therefore, the separation amount w(1) and recovery amount wr(1) of the compound of interest can be determined by carrying out the computation of the above equilibrium expression by giving fC, H, S and Hr and a hypothetical value of br(p) as operation conditions on the condition that the relation represented by fC=w(1)+wr(1), that is, fC+br(p)=w(1)+b(m+n) is established and by causing the computer to control the hypothetical value so that two values of b(m) which is the amount of a sample substance in the solid phase at the sample solution injection portion of the separation unit and obtained by computing from both upward and downward directions should agree with each other.

It is possible to know conditions for recovering the substance to be separated as W(1) or Wr(1) by changing operation conditions and making simulation so that the result obtained by this computation becomes a required recovery rate. Therefore, when a mixture of two substances is used as a sample, it is possible to simulate with a computer conditions for, discharging one of them as W(1) and the other as Wr(1) at a high purity and to carry out separation using conditions for obtaining the best results.

The material used in the solvent containers and the powder containers of the present invention preferably has resistance against the solvent used and the organic compound to be separated, that is, swelling resistance and corrosion resistance, as exemplified by stainless steel, glass and plastics (such as Teflon). Requirements for the material of the powder containers and the solvent containers as shown in FIGS. 2(a)–(b), 3(a)–(c) and 4(a)–(b), for example, when the outer side wall of the powder container and the inner wall of the solvent container are brought into close contact with each other through a liquid thin film is preferably such that, in addition to the above conditions, the outer side wall of the powder container and the inner wall of the solvent container are easily formed with accuracy, for example, stainless steel.

The filter net for separating the powders from the solvent is made from a material which can be easily machined, such as stainless steel or glass. It is, for example, fine porous stainless steel or glass filter, or a stainless steel wire or fiber.

The pipe for moving the solution of the organic compounds to be separated and the separated solvent is made from commonly used expansion resistant and corrosion resistant stainless steel, glass or Teflon.

BRIEF DESCRIPTION OF THE DRAWINGS

FIGS. 2(*a*) and 2(*b*) are views showing a solvent container, in which: FIG. 2(*a*) is a top view of the solvent container when the mixing and separation (solid-liquid separation) of the powders and the solvent are carried out by a pressure difference between the powder side and the solvent side of a filtration unit in the powder container; and FIG. 2(*b*) is a front view (sectional view of a left half) of the solvent container in FIG. 2(*a*);

FIGS. 3(*a*) to 3(*c*) are views showing a powder container, in which: FIG. 3(*a*) is a top view of the powder container corresponding to the solvent container in FIG. 2(*a*); FIG. 3(*b*) is a front view (sectional view of a left half) of the powder container in FIG. 3(*a*); and FIG. 3(*c*) is a side view of the powder container in FIG. 3(*a*);

FIGS. 4(*a*) and 4(*b*) are views showing the solvent container and the powder container, in which: FIG. 4(*a*) is a top view of the powder container in FIGS. 3(*a*) to 3(*c*) placed in the solvent container in FIGS. 2(*a*) and 2(*b*); and FIG. 4(*b*) is a side view (sectional view of a left half) of the powder container in FIGS. 3(*a*) to 3(*c*) placed in the solvent container in FIGS. 2(*a*) and 2(*b*). A right half of the figure is a sectional view of the solvent container alone and a side view of the powder container;

FIGS. 5(*a*) to 5(*c*) are perspective views from the side of the solvent container when the solvent passes through a filtration unit of the powder container for solid-liquid extraction and the separation of the powders from the solvent (solid-liquid separation) is carried out by giving a pressure difference or centrifuging and giving a pressure difference as required. The powder container is placed in the solvent container, in which: FIG. 5(*a*) shows that the powders and the solvent are mixed together; FIG. 5(*b*) shows a state after the powder container is raised above the liquid surface of the solvent in the solvent container and centrifuged (the solvent is then squeezed out by pressurizing air from the powder container side as required); and FIG. 5(*c*) shows a groove 126 for moving vertically a projection on the outer wall of the powder container which reciprocates at the time of extraction and supports the powder container at the time of centrifugation, and also shows a lead-in groove 127 for supporting the projection;

FIGS. 6(*a*) and 6(*b*) are diagrams of the powder container when the powders and the solvent are mixed together in the powder container for extraction between solid phase and liquid phase and then the powders and the solvent are centrifuged. A powder pool 135 is formed in the bottom. A filtration unit 133 is provided as required, in which: FIG. 6(*a*) is a side perspective view of the container; FIG. 6(*b*) is a top view of the container;

FIG. 7(*b*) is a top view of the container;

FIGS. 8(*a*) to 8(*c*) show a flow of solid-liquid extraction operation when the powder container of FIGS. 6(*a*) and 6(*b*) or FIGS. 7(*a*) and 7(*b*) is used. Arrows show the moving directions of the solvent (solution), in which: FIG. 8(*a*) shows that partition equilibrium between solid phase and liquid phase is attained in the powder container 13. The solvent container is empty at this point; FIG. 8(*b*) shows that the solvent is moved to the paired solvent container 12 for the next extraction between solid phase and liquid phase by centrifuging the powders and the solvent after the first partition equilibrium between solids and liquid phase is attained. The means of moving is a transfer pipe (unshown) or inclination. The solvent is moved through the filtration unit provided from the inner wall of the powder container toward the center direction or the filtration unit provided in the transfer pipe (unshown) to prevent the powders in the powder container from being moved to the solvent container together with the solvent as required; and FIG. 8(*c*) shows that the solvent is moved to the paired powder container for the next extraction between solid phase and liquid phase. If required, as the movement takes place, the solvent is passed through the filtration unit provided in the powder container from the outside of the powder container. Thereby, the powders collected at the filtration unit by the transfer of the solvent after the previous extraction between solid phase and liquid phase are sent back to the solid-liquid extraction portion in the powder container.

Description of Reference Symbols

Figure 5:
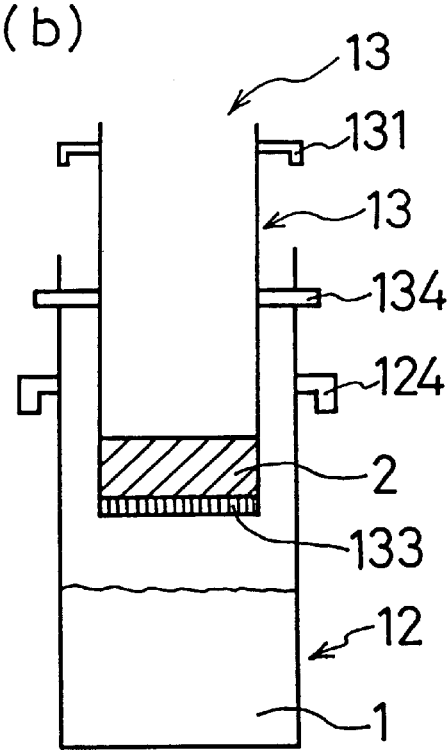
Figure 5:
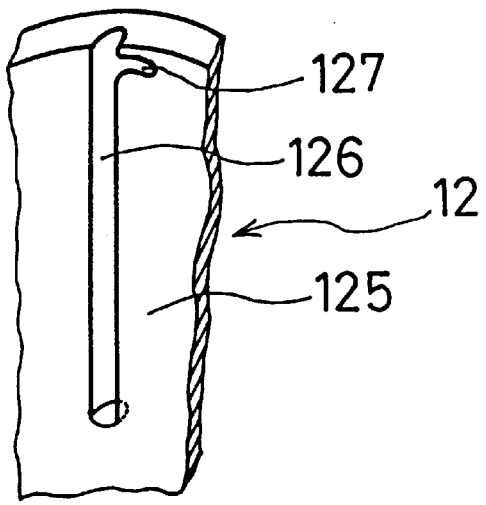
Figure 6:
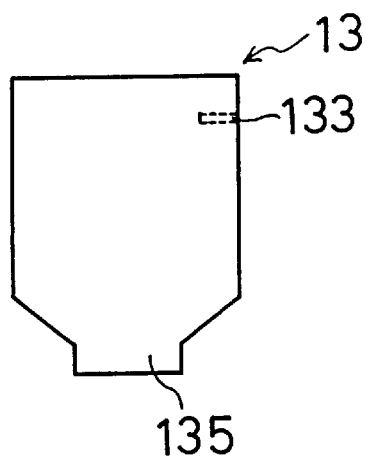
Figure 6:
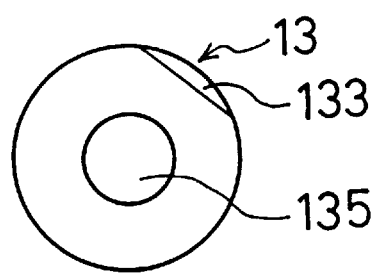
Figure 7:
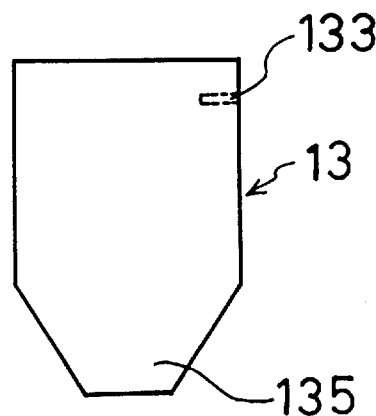
FIGS. 7(*a*) and 7(*b*) are diagrams of the powder container when the powers and the solvent are mixed together in the powder container for extraction between solid phase and liquid phase and then the powders and the solvent are centrifuged. The powder pool 135 is formed in the bottom. The filtration unit 133 is provided as required, in which FIG. 7(*a*) is a side perspective view of the container.
Figure 7:
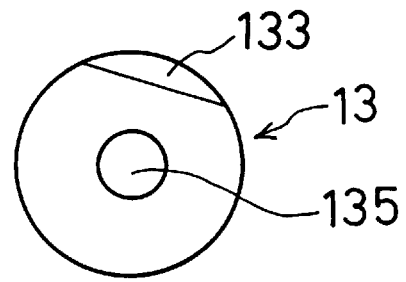
Figure 8:
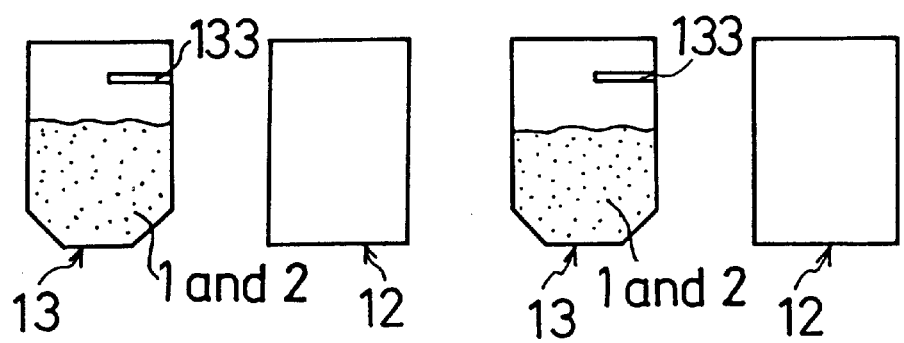
Figure 8:
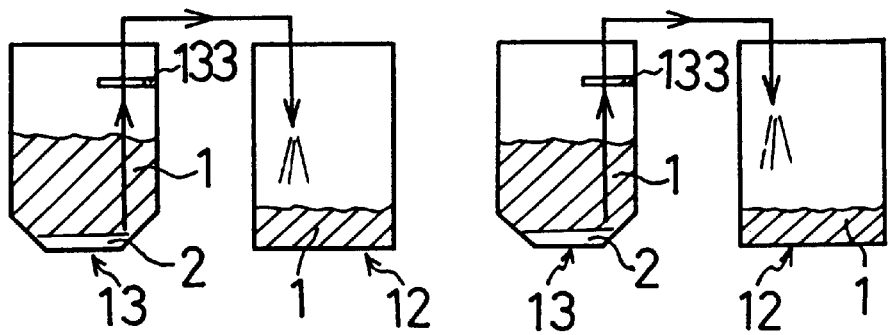
Figure 8:
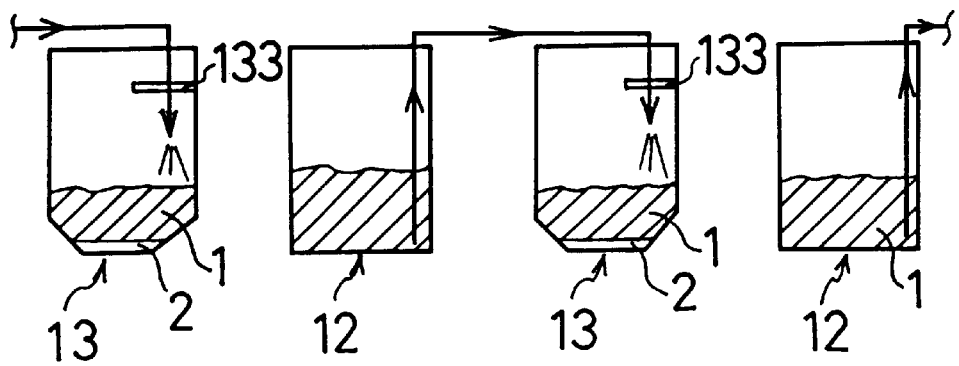

P1 . . . pump for separation solvent, P2 . . . pump for sample solution, P3 . . . pump for separation solvent after (m+n) times of partition equilibrium, P4 . . . pump for solvent for eluting components adsorbed to powders, P5 . . . pump for solvent which has eluted components adsorbed to powders, 1 . . . solvent, 2 . . . powders, 11 . . . new separation solvent container, 12 . . . solvent container, 12 (1, . . . , m, . . . or m+n) . . . solvent container for each stage of partition equilibrium, 12 (0) . . . empty solvent container (after the solvent is removed after (m+n) times of partition equilibrium), 121 . . . looped belt-like recess for circulation of solvent, 124 . . . grip for supporting solvent container at the time of centrifugation, 125 . . . inner wall of solvent container, 126 . . . groove for reciprocating, moving and supporting projection on the outer wall of powder container for supporting powder container at the time of reciprocation and centrifugation during extraction, 127 . . . lead-in groove, 13 . . . powder container, 13 (1, . . . , m, . . . or m+n) . . . powder container for each stage of partition equilibrium, 131 . . . grip used for vertical reciprocation of powder container, 132 . . . hole for circulation of solvent, 133 . . . filtration unit, 134 . . . grip (or projection) for supporting powder container at the time of centrifugation (bendable structure in FIGS. 5(*a*) and 5(*b*) (FIG. 5(*a*) shows when it is bent and FIG. 5(*b*) shows when it is stretched)), 135 . . . powder pool, 136 . . . sealing material (made from fluororesin), 14 . . . sample solution container, 15 . . . storage container for separation solvent after partition equilibrium, 21 . . . new eluting solvent storage container, 22 (1, . . . or p) solvent container for each stage of elution, 22(0) . . . empty solvent container or new solvent container (after solvent is removed from solvent container after p times of elution of components adsorbed to powders), 23 (1, . . . or p) . . . powder container for each stage of elution, 23(p+1) . . . powder container after p times of elution of components adsorbed to powders, recovered powder container or new powder container, 25 . . . storage container for solvent after elution of components adsorbed to powders.

DETAILED DESCRIPTION OF THE PREFERRED EMBODIMENTS

EXAMPLE 1

Figure 1:
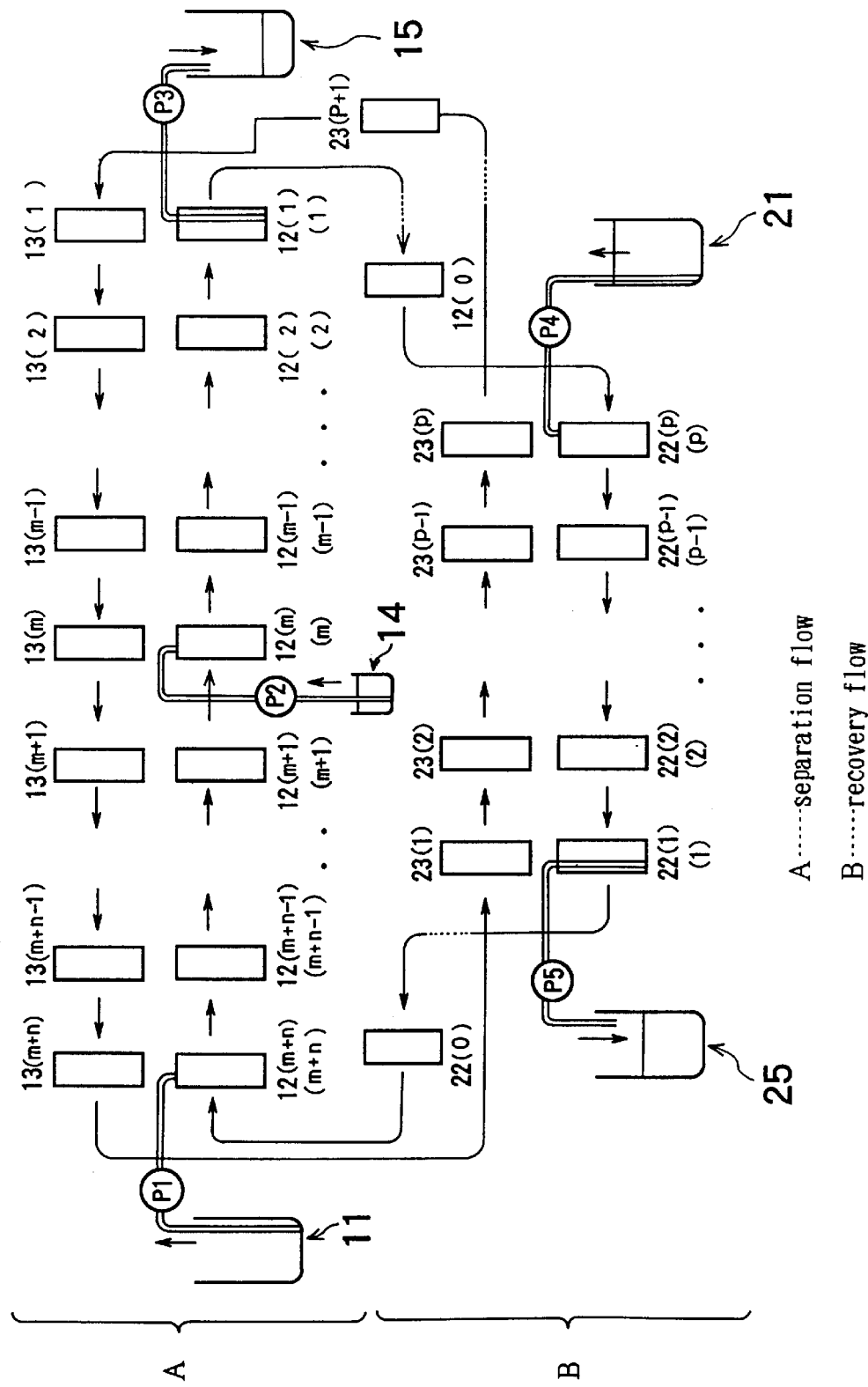
FIG. 1 shows the scheme of countercurrent extraction between solid phase and liquid phase when the number of stages of partition equilibrium is (m+n). Numbers 1 to (m+n) for containers are the numbers of partition combinations of powder containers 13 (upper row) and solvent containers 12 (lower row) used to attain partition equilibrium at that time. Numbers 1 to p for containers are the numbers of partition combinations at that time of powder containers 23 (upper row) and solvent containers 22 (lower row) for eluting components adsorbed to powders from the powders which has gone through the step of partition equilibrium. Arrows show the moving directions of the containers.
Figure 2:
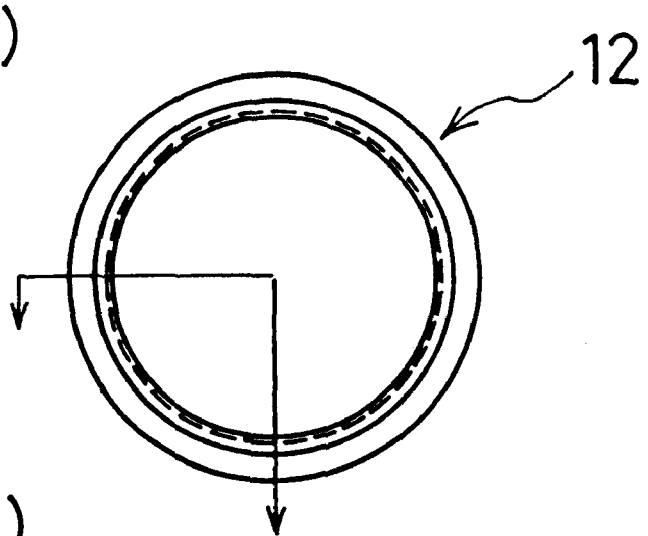
Figure 2:
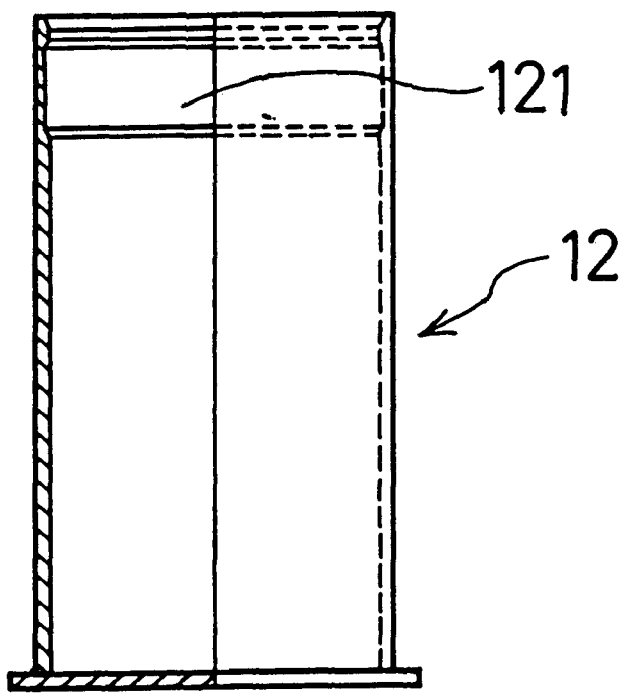
Figure 3:
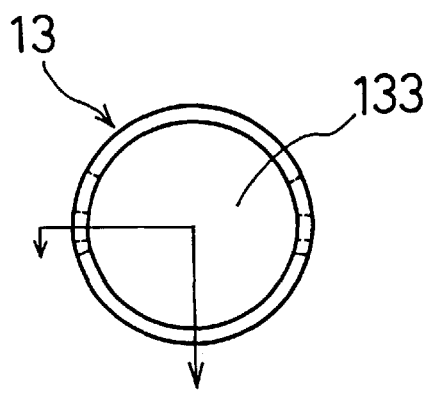
Figure 3:
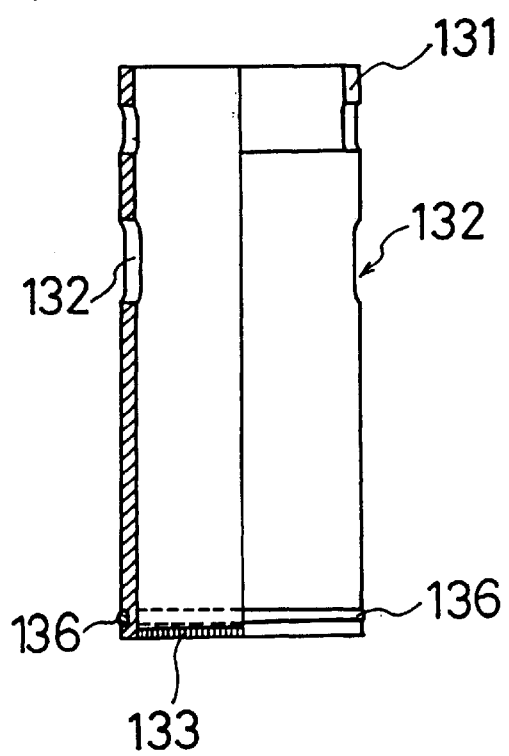
Figure 3:
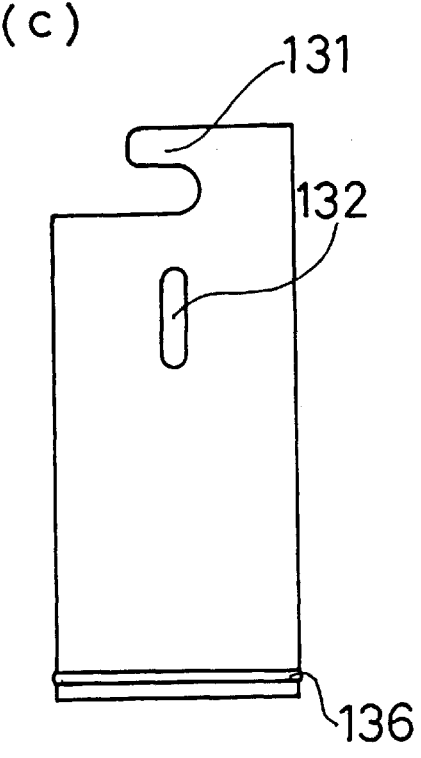
Figure 4:
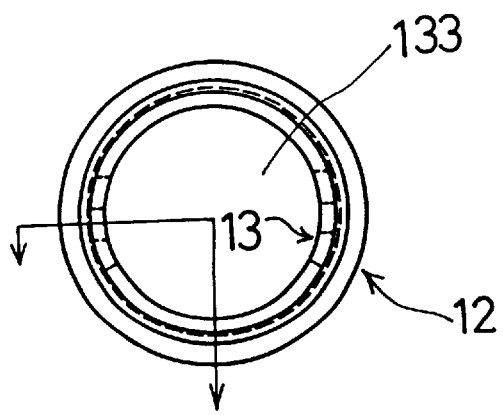
Figure 4:
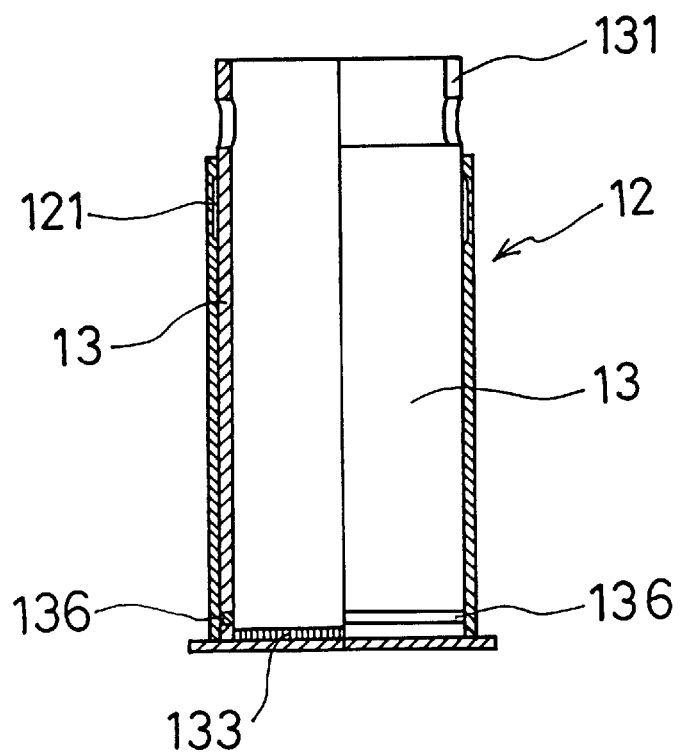

Example 1 of the present invention will be described with reference to FIG. 1. FIG. 1 shows the scheme of solid-liquid countercurrent extraction when the number of stages of partition equilibrium is (m+n). This scheme is divided into a multi-stage solid-liquid separation flow for separating sample components and a recovery flow for eluting the separated sample components from powders and regenerating the powders.

Numbers 1 to (m+n) for the containers of the separation flow are the numbers of partition combinations at a given time of powder containers 13 (upper row) and solvent containers 12 (lower row) used to attain partition equilibrium. Numbers 1 to p for the containers of the regeneration flow are the numbers of partition combinations of powder containers 23 (upper row) and solvent containers 22 (lower row) at a given time for eluting components adsorbed to powders from the powders which went through a partition equilibrium step. Arrows show the moving directions of the containers.

First, each of the solvent containers is filled with the same predetermined amount of the same solvent and each of the powder containers is filled with the same predetermined amount of powders moistened with a predetermined amount of the above solvent. When the following multi-stage partition between solid phase and liquid phase is carried out a predetermined number of times, this multi-stage solid-liquid partition system is stabilized and becomes a multi-stage solid-liquid partition system in which each component of a sample to be analyzed has a fixed concentration gradient.

(a) A predetermined amount of a sample solution is injected into an m-th solvent container 12(m) from the right from a sample solution container 14 through a pump P2 for the first partition between solid phase and liquid phase. The solvent in the solvent container 12 and the powders in the powder container 13 having the same number as that of the solvent container 12 are mixed together to carry out solid-liquid extraction. After the end of the first partition between solid phase and liquid phase, the powders and the solvent in all the powder containers and the solvent containers are mixed together and stirred by coupling the powder containers and the solvent containers of the same numbers with each other from the right in the rows. When partition equilibrium between solid phase and liquid phase is attained by contact between the solvent and the powders in the powder container of each pair, the powders and the solvent in the powder container of each pair are separated from each other, the solvent is returned to the solvent containers, and then the two interconnected rows are separated from each other, thereby the first (m+n)-stage partition between solid phase and liquid phase being completed.

(b) Thereafter, the row of the powder containers moves by one stage to the left and a new powder container (may be a powder container 23(p) regenerated from the recovery flow) is added to the right end of the row of the powder containers as a powder container 13(1). The powder container in which sample components have already been separated is removed from the left end of the row of the powder containers, thereby a new row of (m+n) powder containers 13 being formed.

The powder container 13(m+n) used for the first partition between solid phase and liquid phase is incorporated into the recovery flow as a powder container 23(1) to elute sample components adsorbed to the powders and regenerate the powders.

(c) After the above sample solution is supplied to the m-th solvent container from the right or without supplying the sample solution for the second partition between solid phase and liquid phase for the (m+n)-stage countercurrent extraction of sample components, the powders and the solvent in all the powder containers and the solvent containers are mixed together and stirred by pairing and coupling the powder containers and the solvent containers of the same numbers with each other from the right in the rows. When partition equilibrium between solid phase and liquid phase is attained by contact between the powders and the solvent in the powder container of each pair, the powders and the solvent in the powder container of each pair are separated from each other, the solvent is returned to the solvent containers, and the two interconnected rows are separated from each other, thereby the second (m+n)-stage partition between solid phase and liquid phase being completed.

(d) Thereafter, the row of the solvent containers moves by one stage to the right, a solvent container filled with a fresh solvent is added to the left end of the row of the solvent containers, and the solvent container in which sample components have already been separated is removed from the right end of the row of the solvent containers, thereby a new row of (m+n) solvent containers being formed.

The separation solvent after the end of partition equilibrium is transferred to a separation solvent container 15 after the end of partition equilibrium through a pump P3 from the solvent container 12(1) for the second partition between solid phase and liquid phase and the empty solvent container 12(1) becomes a solvent container 12(0). The solvent container 12(0) is incorporated into the recovery flow line and can be regenerated as a solvent container 22(p).

The recovery flow is a p-stage solid-liquid partition system. The incorporated powder container removed from the above partition flow is caused to flow countercurrently to a solvent container filled with a fresh and the same solvent as the solvent used in the partition flow to carry out multi-stage partition between solid phase and liquid phase, the adsorbed sample components are eluted from the powders in the powder container, and the powders are regenerated. A powder container 23(p+1) which contains regenerated powders is incorporated to the right end of the partition flow as a powder container 13(1). The solvent containing the eluted sample components is injected into a solvent container 25 through a pump P5.

The solutions in the solvent containers 15 and 25 are purified by the same method or different commonly used methods, such as concentration, recrystallization or chromatography.

EXAMPLE 2

A description is subsequently given of the powder containers and the solvent containers when partition equilibrium according to the method of the present invention and the mixing and separation of the powders and the solvent (solid-liquid separation) are carried out by a pressure difference between the powder side and the solvent side of the filtration unit of the powder container with reference to FIGS. 2(a) to 4(b).

FIGS. 2(a) and 2(b) show the solvent container 12. The solvent container 12 is generally a bottomed cylinder. After the solvent is injected into the solvent container 12, the powder container 13 filled with the powders is placed in the solvent container 12 and reciprocated vertically. The inner cylindrical wall of the solvent container 12 and the outer side surface of the powder container 13 are in close contact with each other through a solvent thin film or a sealing material provided at a lower portion of the outer side wall of the powder container 13 or an upper portion of the inner wall of the solvent container 12. A looped belt-like recess 121 for the circulation of the solvent moving upward from this close contact portion into the powder container 13 is formed in the solvent container 12 such a manner that it increases the inner diameter of the inner wall like a belt.

FIGS. 3(a) to 3(c) show the powder container 13. The side of the powder container 13 is cylindrical so that it can get into close contact with the inner wall of the solvent container 12 through a solvent thin film. A porous filtration unit 133 through which the solvent 2 can pass but the powders 2 cannot pass is provided in the bottom of the cylinder. The filtration unit 133 is generally a porous glass filter formed by melting glass powders or fibers or a net produced from plastic fibers, glass fibers, metal fibers or finely thin wire.

The containers 12 and 13 of FIGS. 2(a) to FIGS. 3(c) are made from generally a metal which is easily formed into a cylinder with accuracy and has corrosion resistance against both the solvent used and the organic compound to be separated and abrasion resistance against reciprocation.

A grip 131 for holding the powder container 13 when it reciprocates in the solvent container vertically is provided at an upper portion of the powder container 13. One or a few (2 in the figure) solvent circulation holes 132 for introducing the solvent from the looped belt-like recess 1 21 for the circulation of the solvent on the inner wall of the solvent container 12 are formed on the side wall.

FIGS. 4(a) and 4(b) show that the powder container 13 is placed in the solvent container 12. When the powder container 13 filled with the powders is inserted into a portion close to the bottom portion of the solvent container 12 filled with the solvent, the inner cylindrical wall of the solvent container 12 and the outer side wall of the powder container 13 get into close contact with each other through a solvent thin film or a sealing material, leaving an air-tight space therebetween, whereby the solvent passes through the filtration unit 133 and contacts the powders with the result that the powders are immersed in the solvent. When the powder container 13 is pulled up by holding the grip 131, the solvent moves to the solvent container 12 through the filtration unit 133. Then, when the powder container 13 is pulled down, the solvent flows into the powder container through the filtration unit 133.

By a repetition of this vertical reciprocation, the solvent 1 and the powders 2 are mixed together in the powder container 13 and partition equilibrium is attained quickly.

Part of the solvent 1 moving upward between the outer side wall of the powder container 13 and the inner wall of the solvent container 12 by a repetition of vertical reciprocation enters the powder container 13 through the looped belt-like recess 121 for the circulation of the solvent and the solvent circulation holes 132.

When the powder container 13 is pulled up farther than the vertical reciprocation distance, a portion below the filtration unit 133 is depressurized, air contained in the powder container 13 is forced out from behind the solvent, and the solvent 1 between the powders 2 on the filtration unit 133 is forced out into the solvent container 12.

In this stage, the solvent container 12 and powder container 13 of each pair are separated from each other by pulling the powder containers 13 from the solvent containers 12. They are arranged to form new combinations for the next stage and the powder containers 13 are inserted into the respective solvent containers 12.

EXAMPLE 3

FIGS. 5(a) to 5(c) are perspective views from the side of the solvent container 12 when the solvent 1 passes through the filtration unit 133 of the powder container 13 for solid-liquid extraction and the separation of the powders 2 from the solvent 1 (solid-liquid separation) is carried out by giving a pressure difference or centrifuging and then, if required, giving a pressure difference. The powder container 13 filled with the powders 2 is placed in the solvent container 12 filled with the solvent 1.

FIG. 5(a) shows that the powders 2 and the solvent 1 are mixed together. Mixing is carried out by the flowing of the solvent 1 caused by the vibration or rocking of the solvent container 12 and/or the flowing of the solvent 1 caused by the relative vertical reciprocation of the solvent container 12 and the powder container 13. In this case, the inner cylindrical wall of the solvent container 12 and the outer side wall of the powder container 13 do not need to be in close contact with each other through a solvent thin film or the like. The movement of the solvent through the filtration unit 133 is carried out by a liquid pressure difference between the solvent container 12 and the powder container 13. Mixing may be carried out by the gas pressurization and gas depressurization of the powder container 12.

FIG. 5(b) shows that, after partition equilibrium between solid phase and liquid phase is attained by mixing the powders 2 with the solvent 1, the powder container 13 is pulled up to such an extent that the lower surface of its bottom portion is located above the liquid surface of the solvent container 13. The solvent between the powders is discharged by pressurizing the powder container 13 with gas, by centrifuging the powder container 13 in the solvent container 12 together with the solvent container 12, or by pressurizing the powder container 13 with gas in addition to centrifugation. The discharge of the solvent by centrifugation or gas pressurization in this Example is carried out in the paired solvent container 12. However, it may be carried out in another container but the collected solvent is returned to the solvent container 12 paired with the powder container 13. After the end of the discharge of the solvent 1 from the powder container 13, the paired solvent container 12 and powder container 13 are separated from each other and a new pair is formed for the next partition equilibrium between solid phase and liquid phase.

The grips 124 of the solvent container 12 and the grips 131 and 134 of the powder container 13 are illustrated in FIGS. 5(a) and 5(b). The grips 124 are used to support the solvent container 12 when the solvent container 12 containing the powder container 13 is centrifuged. The grips 124 can freely rotate around the horizontal extension axis of the grips on a base supporting the grips (not shown) and thereby can freely change the inclination of the solvent container 12 at the time of centrifugation. The two grips 124 of FIGS. 5(a) to 5(c) are located at a relatively upper position of the outer cylindrical side wall on opposite sides. Thereby, the solvent 1 in the solvent container 12 can be located in a centrifugal direction at the time of centrifugation.

The grips 131 are located at a relatively upper portion of the powder container 13 and used to vertically reciprocate the powder container 13 and/or rock the powder container 13 in the solvent container 12. The grips 134 are located at a central portion or a lower portion of the powder container 13 and used to vertically reciprocate the powder container 13 or used when the powder container 13 is pulled up to such an extent that the under surface of its bottom portion is located above the liquid surface of the solvent container 13 and supported on the upper side wall of the solvent container 12 (part including a tip of the grip 134 can change its direction to a horizontal direction above the upper side wall of the solvent container 12 when the powder container 13 is supported on the upper side wall). The grips 134 are merely a projection extending in almost a horizontal direction and having a different shape from that shown in the figures. The projection moves vertically in a groove 126 illustrated in FIG. 5(c) at the time of partition equilibrium and is introduced into a lead-in groove 127 at the time of centrifugation to support the powder container 13. Two grips 131 and two grips 134 are provided and the two in each set are located on the outer side wall of the cylinder on the opposite sides. The grooves 126 and the lead-in groves 127 are located at positions 125 (on the inner wall of the solvent container at opposite positions) where the grips 134 can move as required. The grips 131 and 134 may be provided at the same time.

EXAMPLE 4

This Example is a method of carrying out solid-liquid separation by centrifugation after solid-liquid partition equilibrium between all the powders and the solvent is attained in the powder containers.

This Example will be described with reference to FIGS. 6(a) to 8(c).

FIGS. 6(a) and 6(b) show the structure of the powder container 13 when the powders and the solvent are mixed together in the powder container 13 and then centrifuged for solid-liquid extraction. A powder pool 135 is formed in the bottom portion. A filtration unit 133 is provided as required.

The filtration unit 133 is provided to prevent the powders in the powder container 13 from entering the solvent container 12 together with the solvent when the supernatant solvent is injected into the solvent container 12 by inclination or passing through a transfer pipe (unshown) after centrifugation is carried out for solid-liquid separation. The filtration unit 133 is provided from the inner wall toward the center direction in the powder container or provided in the transfer pipe.

FIGS. 7(a) and 7(b) show another example of the powder container 13 for the same purpose as that of the powder container 13 shown in FIGS. 6(a) and 6(b).

FIGS. 8(a) to 8(c) show a solid-liquid extraction operation flow when the powder container shown in FIGS. 6(a) and 6(b) or FIGS. 7(a) and 7(b) is used.

FIG. 8(a) shows that solid-liquid extraction is carried out in the powder container 13. In this case, the solvent and the powders can be stirred by vibration or a stirrer. The solvent container 12 is empty.

FIG. 8(b) shows that the solvent is moved to a solvent container of another pair for the next solid-liquid extraction by the centrifugation of the powders and the solvent after the end of the first solid-liquid extraction. The means of moving the solvent is passing through a transfer pipe (unshown) or inclination. The solvent is moved through the filtration unit provided from the inner wall of the powder container 13 toward the center direction or provided in the transfer pipe (unshown) as required to prevent the powders in the powder container 13 from entering the solvent container 12 together with the solvent.

FIG. 8(c) shows that the solvent is moved to the paired powder container 13 for the next solid-liquid extraction. The solvent is passed through the filtration unit provided in the powder container from the outside of the powder container as required. Thereby, the powders collected in the filtration unit by the transfer of the solvent after the previous solid-liquid extraction are sent back to a solid-liquid extraction portion in the powder container.

Back to the state shown in FIG. 8(a) above, partition equilibrium between solid phase and liquid phase is attained.

EXAMPLE 5

Separation is carried out under the following separation conditions (see FIGS. 1 to 4(b)). (Partition conditions are obtained by measuring the partition rate through preliminary experiments.)

[solvent] type:toluene: butanol=1:1 (w/w), weight in each stage: 40 g

[powders] type: silica gel for column, mesh (particle size): 75 to 150 µm, weight in each stage: 11 g

[sample to be separated] type: caffeine and theophylline (caffeine:theophylline=1:1 (w/w), concentration C=1 (mg/g of solvent), amount of each addition: 40 mg of sample, 40 g of solvent solvent container 12 used: inner diameter of 50 mm$\phi$, height of 100 mm powder container 13 used: inner diameter of 45 mm$\phi$, outer diameter of 49.8 mm∠, height of 120 mm, 20 µm in pore diameter of filtration unit, stainless steel for material of filtration unit number of partition stages (m+n): 7 stage number (m) to which sample is added: m=4 number of times of sample addition: 1 time per cycle number of times of reciprocation required to attain partition equilibrium: 5 times of vertical reciprocation (about 1 minute in total)

operation (partition) temperature: normal temperature moving of powder container and solvent container after sample addition and partition: repetitions of addition of sample solution to solvent container (4), one time of solid-liquid partition equilibrium, moving row of paired separated powder containers, one time of partition equilibrium between solid phase and liquid phase and moving row of paired separation solvent containers.

The circulation of the solvent from the solvent container to the powder container through the looped belt-like recess (121) for the circulation of the solvent and the solvent circulation holes (132) at the time of partition was satisfactory.

After purification using the 7-stage partition, the purified caffeine was partitioned in the powder container 13(7) and the purified theophylline was discharged into the solvent container 12(1). The purified caffeine in the powders is eluted by the same solvent as that used for separation.

Purification result obtained by multi-stage partition between solid phase and liquid phase: larger than 90% of each sample substance was recovered at a purity of 95.4 to 94.7%. This shows that separation at a higher purity can be carried out by increasing the number of partition stages and proves that this separation means has practical effectuality. In order to increase the recovery rate, the amount of the recovery solvent must be increased and/or the number of recovery stages must be increased.

It is assumed that the same result can be obtained as a matter of course even when the separation of the powders from the solvent is carried out by centrifugal force.

EXAMPLE 6

An apparatus was constructed by looping 12 pairs of solvent containers and powder containers described in Example 5 and experiments on separation and recovery were conducted using 8 pairs out of the 12 pairs for separation and another 4 pairs for recovery.

As for an extraction system, 1.7 g of chemically formed 300–75 gel ODS (particle diameter of 40 to 100 μm) was used as powders and a mixture of 1-propanol and water (1-propanol: water=2:8) was used as a solvent. 18.8 g of the solvent was used for separation and 54.8 g of the solvent was used for recovery.

Samples to be separated were methyl ester p-hydroxybenzoate (partition coefficient of 6.2) and propyl ester p-hydroxybenzoate (partition coefficient of 22.3).

When 1.0 ml of a sample solution containing the above sample substances in a concentration of 4.1 mg/ml each was added for each cycle of extraction partition operation to the 4-th (m=5) pair solvent container from the left and extraction separation operation was carried out 40 times repeatedly, 66.04 mg of methyl ester and 0.78 mg of propyl ester (calculation value: 63.10 mg of methyl ester, 0.63 mg of propyl ester) were collected into a separation solution and 3.82 mg of methyl ester and 88.82 mg of propyl ester (calculation values: 2.52 mg of methyl ester, 85.31 mg of propyl ester) were collected in a recovery solution. It was confirmed that these values almost agree with calculated values and that the injected sample substances are in good agreement with calculation results in the cylinders of the respective apparatuses and it was proved that the apparatuses operate as expected.

The results of the experiments show that a separation apparatus for effective preparation can be obtained by increasing the number of partition stages of the apparatus to improve separation capability.

INDUSTRIAL UTILITY

According to the separation method of the present invention, an organic compound can be purified with a relatively small number of stages of partition equilibrium and powders for chromatography can be easily recovered and recycled. The separation of an organic compound can be carried out by easily setting advantageous separation conditions through the computer simulation of the numerical expression 1.

What is claimed is:

1. A separating apparatus for carrying out (m+n)-stage solid-liquid countercurrent extraction many times continuously, the apparatus comprising:
   a row of (m+n) powder containers filled with stationary phase powders for chromatography, a new powder container being able to be added adjacent to the right side of a first powder container from the right of the row and a (m+n)-th powder container from the right being able to be removed simultaneously with, before or after the addition of the new powder container;
   a row of (m+n) solvent containers filled with a solvent, a new solvent container being able to be added adjacent to the left side of a (m+n)-th solvent container from the right of the row and a first solvent container from the right being able to be removed simultaneously with, before or after the addition of the new solvent container;
   a sample feed device for supplying a sample solution consisting of the same solvent as the above solvent and two or more components to be separated to an m-th solvent container from the right of the row of the solvent containers;
   a powder container feed device for supplying the new powder container to the right end of the row of the powder containers;
   a powder container removing device for removing a powder container from the left end of the row of the powder containers;
   a solvent container feed device for supplying the new solvent container to the left end of the row of the solvent containers; and
   a solvent container removing device for removing a solvent container in which the sample components have been separated from the right end of the row of the solvent containers, wherein
   the apparatus repeats the following stages (a), (b), (c) and (d) a required number of times,
   (a) a stage in which the sample solution is supplied to the m-th solvent container from the right for the first solid-liquid partition for the (m+n)-stage countercurrent extraction of the sample components, the powders and the solvent are mixed and stirred by pairing and coupling all the powder containers and the solvent containers of the same numbers from the right in the rows with each other, when partition equilibrium between solid phase and liquid phase is attained by contact between the solvent and the powders in each of the paired powder containers, the powders and the solvent in each of the paired powder containers are separated from each other and the solvent is returned to its solvent containers, and the two interconnected rows are separated from each other to complete the first (m+n)-stage partition between solid phase and liquid phase;
   (b) a stage in which the row of the above powder containers moves to the left by one stage, one new powder container is added to the right end of the row of the powder containers, and a powder container in which sample components have been separated is removed from the left end of the row of the powder containers, thereby forming a new row of (m+n) powder containers;
   (c) a stage in which after the above sample solution is supplied to the m-th solvent container from the right for second solid-liquid partition for the (m+n)-stage countercurrent extraction of the above sample components or without supplying the sample solution, the powders and the solvent are mixed and stirred by pairing and coupling the powder containers and the solvent containers of the same container numbers from the right in the rows with each other, when partition equilibrium between solid phase and liquid phase is attained by contact between the solvent and the powders in each of the paired powder containers, the powders and the solvent in each of the paired powder containers are separated from each other and the solvent is returned to its solvent containers, and the two interconnected rows are separated from each other to complete the second (m+n)-stage partition between solid phase and liquid phase; and
   (d) a stage in which the row of the solvent containers moves to the right by one stage, one new solvent container is added to the left end of the row of the solvent containers, and a solvent container in which sample components have been separated is removed from the right end of the row of the solvent containers, thereby forming a new row of (m+n) solvent containers.

2. The apparatus according to claim 1, wherein further a new powder container is connected to the right side of the new powder container mentioned above and/or further a new solvent container is connected to the left side of the new solvent container mentioned above.

3. The apparatus according to claim 1, wherein the powder container comprises a filtration unit in its lower portion and can be placed in the solvent container or taken out from the inside of the solvent container, and contact between the powders in the powder container and the solvent in the solvent container is carried out by placing the powder container in the solvent container, the solvent in the solvent container enters the powder container and is discharged from the powder container through the filtration unit, the mixing and stirring of the powders and the'solvent are carried out by the reciprocation of the powder container in the solvent container, and the powders are separated from the solvent by the filtration unit.

4. The apparatus according to claim 3, wherein the filtration unit is provided in the bottom portion of the powder container, the powder container and the solvent container are both a bottomed cylinder, at least part of the outer side wall of the powder container and at least part of the inner side wall of the solvent container are in close contact with each other like a looped belt and perpendicularly to the axis of the cylinder so that the solvent container side of the filtration unit of the powder container can be made airtight, the inner side wall and the outer side wall can slide and reciprocate at the close contact portion, the solvent in the solvent container can pass through the filtration unit of the powder container by the reciprocation, and the powders on the filtration unit can be separated from the solvent by a pressure difference between the solvent side and the powder side of the filtration unit.

5. The apparatus according to claim 4, wherein the inner wall of the solvent container, on which the looped belt-like contact portion passes, has a looped belt-like recess at a possible highest portion of the wall to prevent the solvent from leaking to the outside through the looped belt-like close contact portion and to circulate a liquid passing through the looped belt-like close contact portion, and the side wall of the powder container has holes at positions higher than the highest liquid level of the solvent during the mixing of the powders and the solvent.

6. The apparatus according to claim 3, wherein the solvent is separated from the powders on the filtration unit of the powder container by centrifugal force.

7. The apparatus according to claim 1, wherein means of interconnecting the powder container and the solvent container to form a pair is a pipe, and the solvent in the solvent container is moved into the powder container or the solvent in the powder container is moved into the solvent container through the pipe by a pressure difference between the containers generated by pressurizing or depressurizing either one of the containers.

8. The apparatus according to claim 1, wherein the separation of the solvent from the powders is carried out by the movement of the supernatant above the powders in the powder container to the solvent container, the supernatant is caused by standing and separating the powder container and/or centrifugation.

9. The apparatus according to claim 8, wherein the powder container has a powder storage groove or hole for storing or precipitating the powders by standing and separation and/or centrifugation on the inner wall of the bottom portion or the inner side wall.

10. A method of separating sample components comprising separating sample components with the apparatus according to claim 1.

11. The method according to claim 10 for eluting sample components immobilized to the powders from the powders in the powder container after the separation of the sample components, using as an elute the same solvent as the solvent used for separating the sample components.

12. The method according to claim 11 which uses as a new powder container a powder container obtained by the method of claim 10 which contains powders after sample components are eluted.

13. The apparatus according to claim 1, wherein the solid phase is a solid phase having an optically resolving function.

14. The apparatus according to claim 13, wherein the liquid phase is a liquid phase containing an optically resolving agent.

Figure 9:
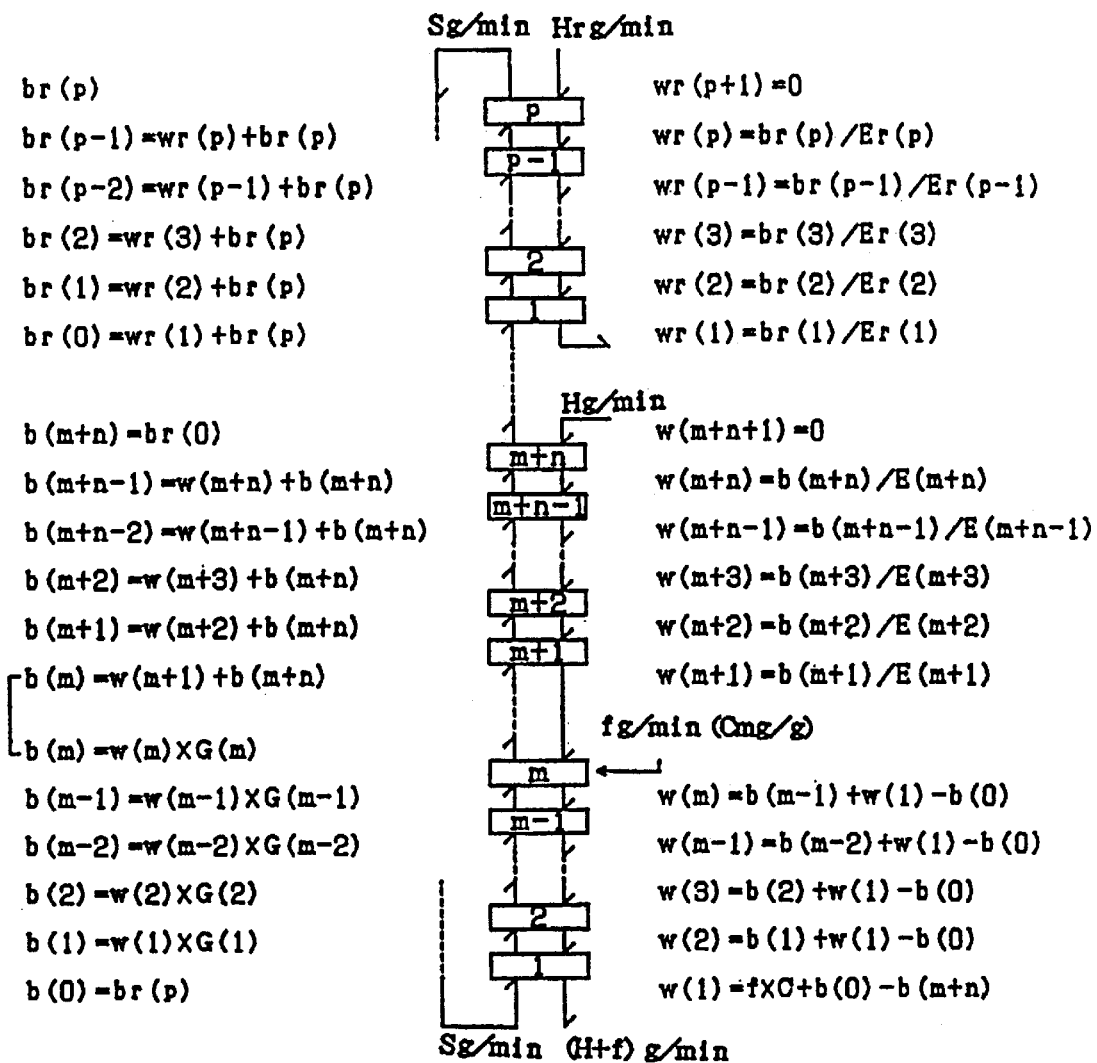
FIG. 9 shows the numerical expression.

15. A method of purifying organic compounds steadily and continuously comprising the steps of:
  repeating multi-stage extraction between solid phase and liquid phase by causing the solid phase and liquid phase to flow countercurrently to each other in the separation unit of a purifying apparatus consisting of the separation unit and a recovery unit so as to separate a mixture of organic compounds into two groups according to partition coefficients between two phases and extract and recover a group of purified organic compound(s) into the solid phase in multiple stages;
  repeating multi-stage extraction between the phases in the recovery unit from the solid phase containing the purified organic compound(s) with another fresh liquid phase than the liquid phase used in the separation unit simultaneously with the above extraction; and
  supplying the solid phase from which the organic compounds have been recovered to the above separation unit to be recycled, wherein:
  the number of stages of extraction in the separation unit is (m+n);
  a sample solution contains an organic compound of interest to be purified and at least one organic compound different from the organic compound, the sample solution to be supplied for each time of extraction contains f g of a solvent which is a liquid phase and the organic compounds of interest to be purified in an amount (single substance) M(mg)=f C(mg) (C mg is the amount of each of the organic compounds based on 1 g of the solvent) and is supplied to the liquid phase of the m-th extraction stage of the separation unit each time extraction is made;
  H g of the solvent which is the liquid phase is supplied to the (m+n)-th extraction stage which is the final extraction stage of the separation unit each time extraction is made;
  S g of the solid phase is supplied to the first extraction stage of the separation unit from the recovery unit each time extraction is made;
  the solid phase discharged from the (m+n)-th extraction stage of the separation unit is supplied as it is to the first stage of the recovery unit;
  the number of extraction stages of the recovery unit is p;
  Hr g of the above another fresh liquid phase is supplied to the p-th extraction stage which is the final extraction stage of the recovery unit each time extraction is made and passes through each extraction stage of the recovery unit and recovers the above purified organic compound(s) from the solid phase by multistage extraction and the Hr g is discharged from the first extraction stage of the recovery unit each time extraction is made;
  S g of the solid phase from which the purified organic compound(s) have been recovered and removed is discharged from the p-th extraction stage which is the final extraction stage of the recovery unit each time extraction is made and supplied to the first stage of the separation unit; and the organic compounds of interest to be purified are purified steadily by setting the ratio of H and S in extraction separation conditions to ensure that the ratio of $Wr(1)$ and $W(1)$ of one of the two organic compounds of interest to be purified satisfy $Wr(1) >> W(1)$ and those of the other organic compound satisfy $Wr(1) << W(1)$, the values $Wr(1)$ and $W(1)$ obtained by the computation of an equilibrium expression which gives the values of partition coefficient at each stage concentration of H, S, f, C, Hr, p, m and n in the equilibrium expression and the compounds of interest to the FIG. 9 extraction equilibrium expression (numerical expression 1) in which the number of estimated extraction stages (m+n) and the partition coefficient $D(n)$ of the organic compounds of interest to be purified between the solid phase and the liquid phase at the concentration of an extraction stage (n-th stage) where the liquid phase is present;

and one of the organic compounds of interest is taken out as $W(1)$ and the other as $Wr(1)$.

\* \* \* \* \*